United States Patent [19]
Manaka

[11] Patent Number: 5,388,443
[45] Date of Patent: Feb. 14, 1995

[54] ATMOSPHERE SENSOR AND METHOD FOR MANUFACTURING THE SENSOR

[76] Inventor: Junji Manaka, c/o Ricoh Seiki Company, Ltd. 1-9-17, Omorinishi Ota-Ku Tokyo 143, Japan

[21] Appl. No.: 82,352

[22] Filed: Jun. 24, 1993

[51] Int. Cl.6 .......................................... G01N 27/12
[52] U.S. Cl. ................................ 73/31.06; 73/29.05; 73/335.03
[58] Field of Search ............... 73/29.05, 31.06, 335.02, 73/335.03, 335.04, 335.05; 338/34, 35

[56] References Cited
U.S. PATENT DOCUMENTS

| | | | |
|---|---|---|---|
| 4,928,513 | 5/1990 | Sugihara et al. | 73/31.06 X |
| 5,048,336 | 9/1991 | Sugihara et al. | 73/29.05 X |

FOREIGN PATENT DOCUMENTS

| | | | |
|---|---|---|---|
| 96549 | 4/1989 | Japan | 73/31.06 |
| 89154 | 4/1991 | Japan | 73/31.06 |

*Primary Examiner*—Thomas P. Noland
*Assistant Examiner*—Joseph W. Roskos

[57] ABSTRACT

A sensor or detector for fluid parameters is in the form of a substrate having at least two cavities and at least two sensing or detecting portions bridging respective cavities. The sensing portions include a first sensing unit which is exposed to the ambient and a second sensing unit which serves a compensating function and is in an air-tight enclosure formed by joining a cover plate with the substrate by a solid adhesive layer formed around the boundary of the second sensing unit. An adhesive tape can be attached to the cover plate to facilitate dicing and separating sensors or detectors that are initially formed on the same substrate.

14 Claims, 6 Drawing Sheets

ATMOSPHERE SENSOR AND METHOD FOR MANUFACTURING THE SENSOR

BACKGROUND OF THE INVENTION

The present invention refers to a sensor and more particularly to one for detecting ambient atmosphere and is related to such devices as gas sensors, humidity sensors, atmospheric pressure sensors and the like.

A conventional gas sensor has been proposed that comprises a metal oxide semiconductor including therein an electrode and a heater serving also as an electrode and capable of sensing ambient atmosphere on the principle that, when the metal oxide semiconductor is heated by the heater, its resistance value drops due to gas absorption by its surface. One problem faced in the application of the gas sensor is that it consumes a large amount of electrical power and is not adaptable to operating with batteries.

To try to solve the above-mentioned problem, a portion projecting into the air such as a bridge structure, cantilever structure or the like, has been provided and a metal oxide semiconductor has been formed thereon to reduce the heating capacity to as low a level as possible and to improve the response time thereby saving on power consumption.

Also a gas sensor having two sensing units with the same construction have been tried, i.e. one which is exposed to ambient atmosphere to detect gas and the another which is entirely shielded from the ambient atmosphere to detect ambient temperature for temperature compensation.

The Japanese publication of unexamined patent applications 3-92754 discloses a complete humidity sensor wherein a first silicon substrate, having two concave portions formed therein, is covered with an insulating protective coat and then provided with two thin film-heating resistors bridged over the respective concave portions thereof and supported thereon.

The above-mentioned sensor is so constructed that heat from the thin-film heating elements of a reduced heat capacity may not directly be transferred to the substrate and the heat's balance may be kept by the spacing formed therein to save on power consumption and to increase its speed of response.

The second substrate has two concave portions formed thereon at places corresponding to those of the first substrate and a notched portion for exposing the pad portion of a thin-film heating resistance.

A bonding glass paste with a low melting point is printed on the substrate by screen-process printing and then a solvent contained in the glass paste is evaporated by temporarily baking it.

The two above-mentioned substrates are opposed to each other in dry air to fill the space of a reference element in such a way that two concave portions of the substrates form two spaces surrounding the respective thin-film heating elements. The substrates are then bonded to each other by heating the glass paste having a low melting point.

The bonded substrates can shut off the reference side's inner space from the outside air and keep a constant ambient atmosphere therein. This ambient atmosphere in the enclosed space may not always be at the proper atmospheric pressure. At the same time, a sensing side inner space is formed in the bonded substrates which has a venting hole formed by utilizing the gap between the joined surfaces of the two substrates.

The newly constructed humidity sensor operates in the following way:

When two thin-film heating elements are supplied with a certain amount of electrical energy, they are self-heated and radiate heat according to the respective amounts of water vapor in their spaces, i.e., the heat conductivity of each space corresponds to the absolute humidity in them and then they reach a constant temperature and represent two different resistance values, the difference of which is detected as the output of an unbalanced potential of a bridge circuit. The absolute humidity can be determined from the detected value.

The above-mentioned -known art, however, has the following drawbacks:

In the forming of the reference space, two semi-conductors are joined by fusing a glass paste with a low melting point, that causes dry air or air with a certain humidity to be heated and thereby to be enclosed as thinned atmosphere in the reference space's chamber. As the result of this, the thin-film heating element cannot sufficiently transfer heat to the charged atmosphere and so its equilibrium temperature rises, making it hard to balance with the sensing portion. Furthermore, considerable time is required to transfer the external ambient temperature to the charged atmosphere thereby affecting the response time. It is also hard to balance the response time with that of the sensing portion.

In addition, the above-mentioned known art provides a shield cover for protecting the sensing and compensating portions from the effect of water used to wash a dicing saw during cutting the semiconductor into the chips. This protection, however, cannot completely protect the sensor because of the electrode pad portion being exposed.

SUMMARY OF THE INVENTION

A primary object of the present invention is to provide a sensor which is simple in construction, easy and inexpensive to manufacture and allows for the minimizing of the internal volume of a sensing portion for temperature compensation and creates an increased response speed.

Another object of the present invention is to provide a sensor which has a sensing portion for temperature compensation which is integrally formed i.e. enclosed with a thin plate and therefore simple in construction, easy and inexpensive to manufacture and capable of quickly responding to a variation in the ambient temperature.

A further object of the present invention is to provide a process for manufacturing a sensor wherein an entire covering member can be air-tightly covered with an adhesive dicing tape to protect against water during the washing procedure for dicing the semiconductor into the chips with a dicing saw.

DESCRIPTION OF THE PREFERRED EMBODIMENTS

Figure 1A:
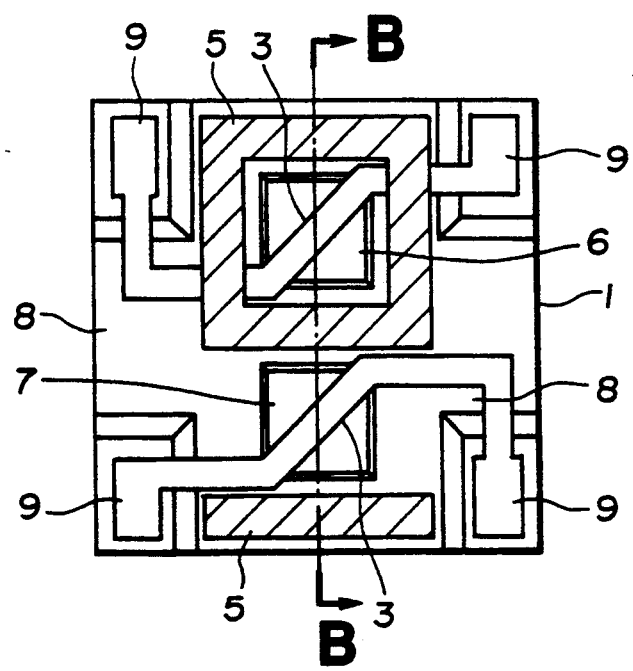
FIGS. 1(a) and 1(b) are views for explaining an example of a conventional flow sensor.
Figure 1B:
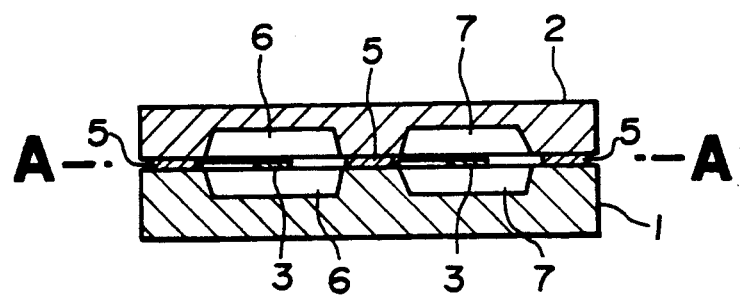

FIGS. 1(a) and 1(b) are, respectively, a plane view taken on line A—A of FIG. 1(b) and a sectional view taken on line B—B of FIG. 1(a) showing an example of an absolute humidity sensor disclosed in the Japanese publication for unexamined patent applications 3-92754.

As shown in FIGS. 1(a) and 1(b), concave portions 6 and 7 for mounting thin-film resistance type heating elements 3 are formed in a first silicon substrate 1, an insulating protective coat is applied over the surface of the substrate 1 and then the heating elements 3 are bridged over the respective concave portions of the substrate and supported thereon.

On a-second substrate 2, two concave portions 6 and 7 forming spaces for mounting the above-mentioned elements ape formed at respective places of the substrate which correspond to those of the first substrate 1, and a notch for exposing the pad portion 9 of a thin film resistance type heating element 3 is also provided. A bonding glass paste 5 of a low melting point is printed according to a pattern showing hatched lines on the substrate 2 by a screen process of printing and then solvent, contained in the glass paste, is evaporated by temporally baking it. Two above-mentioned substrates opposed in dry air or air of a known humidity for filling a space of a reference element in such a way that the two concave portions of the substrates form two spaces surrounding the respective thin-film heating elements. The substrates 1 and 2 are then bonded to each other by heating the glass paste having a low melting point.

Thus, bonded substrates can shut off the reference-side inner space 6 from the external air and always keep a constant ambient atmosphere therein. This ambient atmosphere in the enclosed space may not always be at the proper atmospheric pressure. At the same time in the bonded substrates is formed a sensing-side inner space 7 which has a vent hole 8 formed by gaps provided at the opposite positions of the joined portion.

Such a constructed humidity sensor operates in the following way:

When two thin film-heating elements are supplied with a certain amount of electrical energy, they are self heated and radiate heat according to respective amounts of water vapor in the reference chamber 6 and sensing chamber 7 respectively, i.e., the heat conductivity of each space corresponding to the absolute humidity. Then they reach a constant temperature and have respective resistance values, the difference of which is detected as the output of the unbalanced potential of a bridge circuit. Absolute humidity can be determined from such a detected value.

The above-mentioned known art, however, has the following drawbacks:

In the forming of the reference space 6, two semiconductors 1 and 2 are joined by fusing glass paste 5 of a low melting point, that causes dry air or air of a certain humidity to be heated and, thereby, enclosed as thinned atmosphere in the reference space chamber 6. As a result of this, the thin-film heating element 3 cannot sufficiently transfer heat to the charged atmosphere and hence its equilibrium temperature rises, making it hard to balance with the sensing side. Furthermore, considerable time is required to transfer the external ambient temperature to the charged atmosphere thereby affecting the response time. It is also hard to balance the response time with that of the sensing portion.

In addition, the above-mentioned known art provides the semiconductor 2 with a shield cover for protecting the sensing portion and the compensating portion from the effect of water used for washing a dicing saw during the semiconductor chip's separation. This protection, however, cannot completely protect the sensor because of the exposed electrode pad portion 9.

In view of the foregoing, the present invention was made to further improve the above-mentioned known art, especially, to make a sensing portion for temperature compensation be air-tightly enclosed with a thin flat plate, and therefore to provide a sensor having an integrally formed sensing portion for temperature compensation, which is simple in construction, easy and inexpensive to manufacture and capable of quickly responding to a change in the ambient temperature.

This invention also provides a process for effectively manufacturing said sensor.

Figure 2:
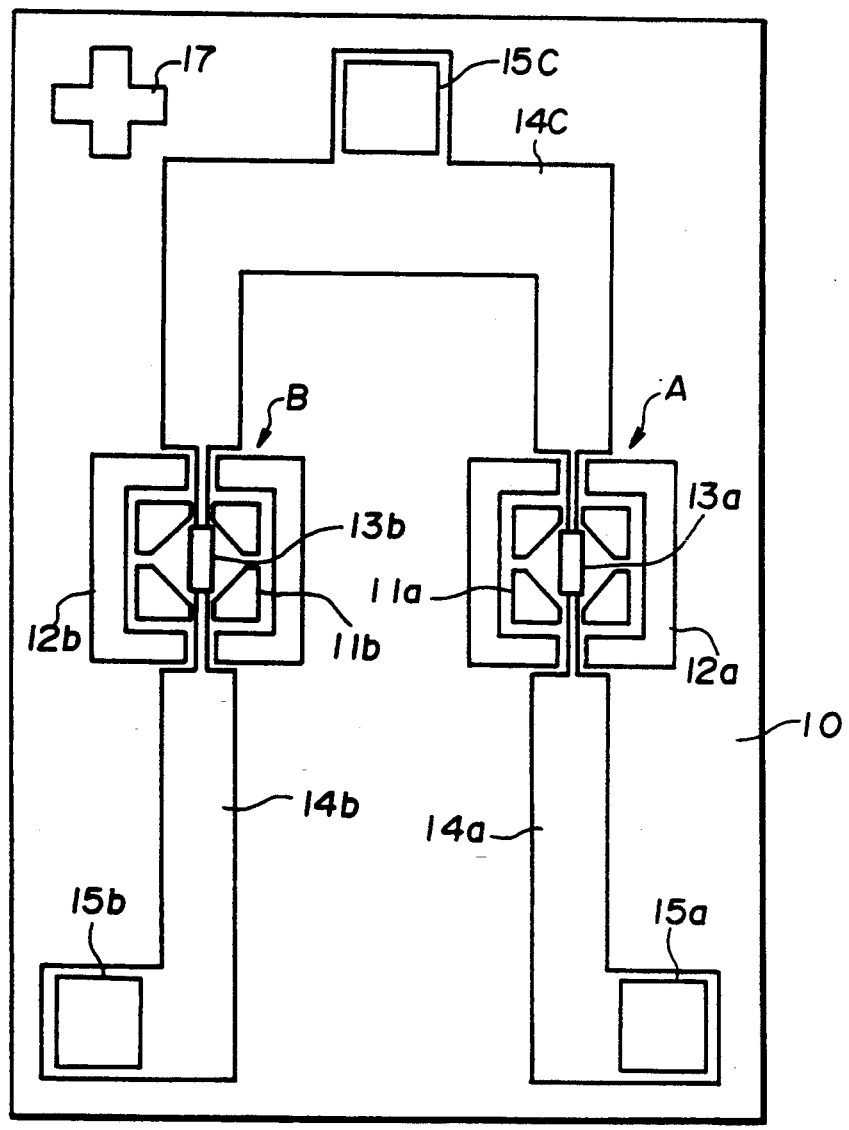
FIG. 2 is a view showing an example of the substrate of a sensor according to the present invention.
Figure 3:
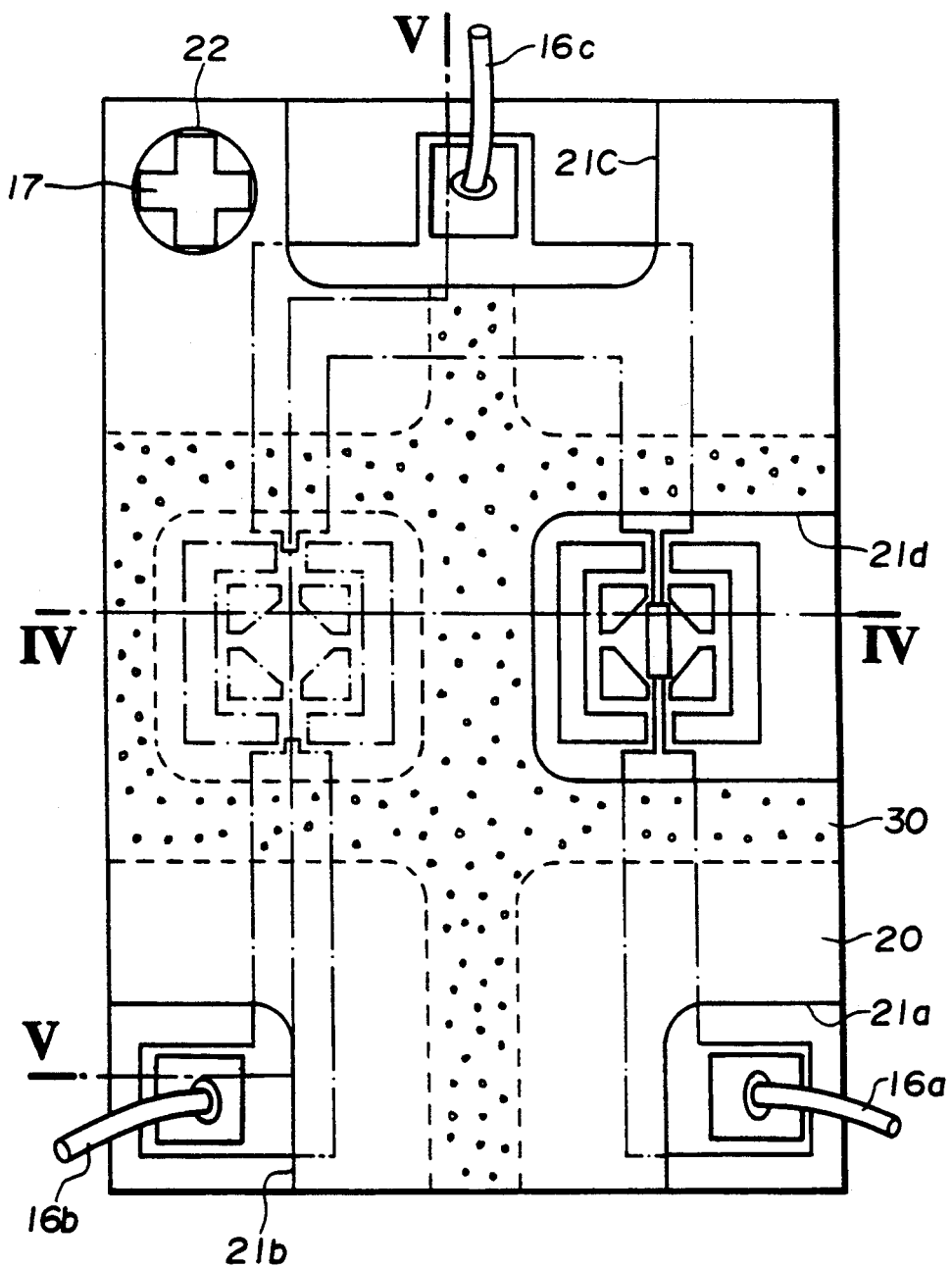
FIG. 3 is a view showing the top surface of a sensor according to the present invention.
Figure 4:
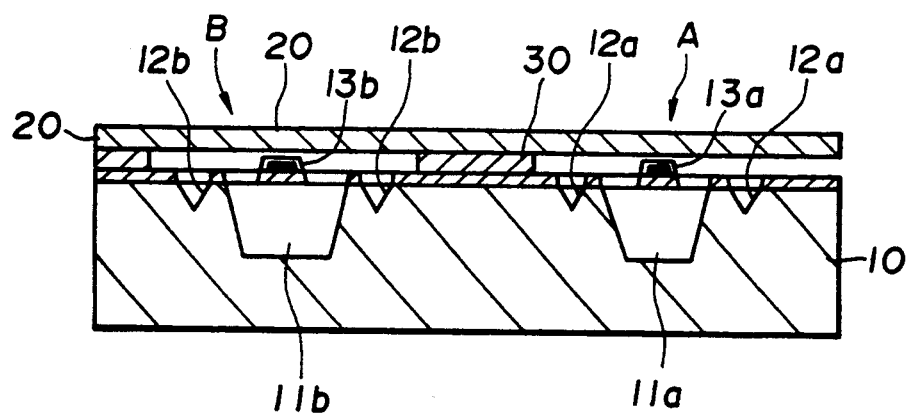
FIG. 4 is a sectional view taken on line IV—IV of FIG. 3.
Figure 5:
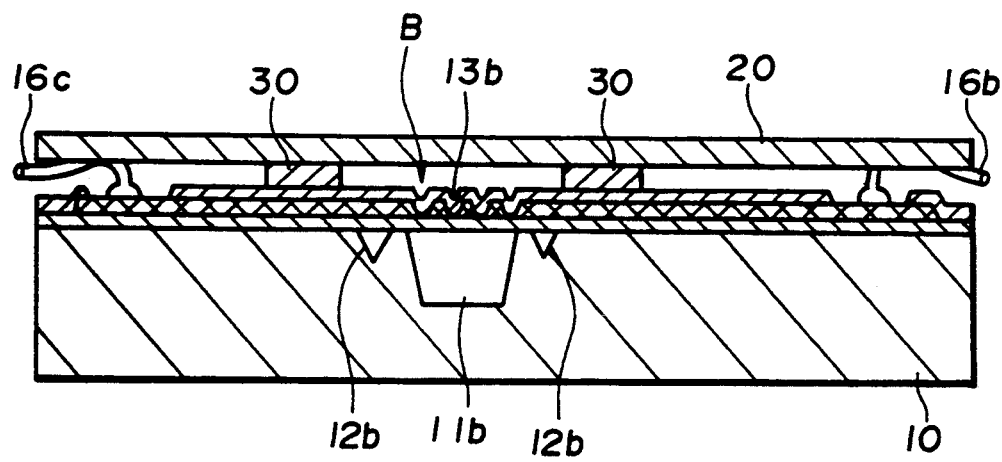
FIG. 5 is a sectional view taken on line V—V of FIG. 3.

FIG. 2 is a construction plane view of a substrate 10 of a sensor according to the present invention, FIG. 3 is a plane view of the substrate 10 provided with a covering member 20 thereon, FIG. 4 is a section taken on line IV—IV of FIG. 3 and FIG. 5 is a section taken on line V—V of FIG. 3. As shown in these drawings, the substrate 10 of the sensor has a gas sensing portion A and a temperature compensating portion B which are provided respectively with cavities 11a and 11b, grooves 12a and 12b, surrounding respective cavities 11a and 11b, sensing elements 13a and 13b bridged over the respective cavities 11a and 11b, electrodes 14a and 14b connected to the respective elements and a common electrode 14c commonly used for the sensing elements, electrode bonding pad portions 15a, 15b and 15c formed at respective electrode terminals exposed thereat, bonding wires 16a, 16b and 16c (see FIG. 3) connected to the respective bonding pads and a registration mark 17 put on a part of the substrate's surface.

FIG. 3 is a plane view showing the above-mentioned sensor's substrate 10 with a covering member 20 bonded thereto. This covering member 20 is a thin plate having notches 21a, 21b and 21c opposite to the bonding wires 16a, 18b and 18c respectively, a notch 21d opposite the gas sensing portion A and a hole 22 opposite the registration mark 17 on the substrate. The covering member 20 is registered on the substrate 10 by matching its resister hole to the registration mark of the substrate and then bonded thereto with adhesive 30. The present invention proposes that the adhesive 30 applied continuously around the periphery of the cavity 11b for the temperature compensating sensing portion so as to entirely enclose the sensing element of the temperature compensating portion B by the substrate 10, the covering member 20 and the adhesive 30 while the gas sensing portion A allows its gas sensing element to be exposed to external atmosphere.

Material of the covering member 20 will be described as follows:

(1) Material of the covering member 20 must satisfy the following requirements:

i) High heat conductivity;

ii) The cover's edge surrounding an electrode shall be low enough not to be touched by the bonding tool tip when wires are being bonded to the electrodes. If the cover has high edges around the electrodes, it is impossible to carry out wire bonding because a tool may hit the edge or be caught thereat when bonding a wire to an electrode or when moving the tool to the other electrode. This is an open package which, differing from general devices, cannot entirely be molded in resin and has exposed bonding wires.

iii) A cover made of Si-wafer can be thinned only to 0.5~0.3 mm. Further thinning of the wafer causes insufficient strength. Thinning the wafer's edge around the electrode requires an additional process.

iv) It is convenient to use sufficiently thin material without additional machining.

v) The material must have a coefficient of thermal expansion similar to that of the substrate to avoid the thermal shift of the bonded cover due to a change in the ambient temperature.

vi) Accordingly, a thin plate of kovar may be a most desirable material, and inbar and inconel are also useful materials of a low coefficient of thermal expansion. Koval of about 0.05 mm in thickness without additional machining can be easily obtained in the market place and is capable of quickly transferring an ambient temperature. The response characteristic of the kovar plate is considerably stable as compared with that of a Si-plate subjected to additional thinning. Material of a large heating capacity cannot serve as a reference element for temperature compensation because it requires time to adapt itself to an ambient temperature.

vii) Other than kovar, the following materials may be used, i.e., stainless steel, nickel (Ni), nichrome (Ni—Cr), or special glass "photoform" (registered trademark) and special ceramics "photoceram" (registered trademark) of The Corning Company, both of which are adaptable to micro-machining. Soft aluminum (Al), lead (Pb), tin (Sn), gold (Au) are also applicable.

viii) The sensor's substrate may have a small deflection in flatness since its surface is coated with films of insulating and heating materials. Accordingly, if the cover does not have flexibility corresponding to the deflection of flatness of the substrate, it may not completely seal the compensating side of the substrate when being registered thereto. It is hard to deflect the silicon (Si) cover according to the surface of the substrate. In this case, the cover shall be subjected to the same process of machining as the substrate. The kovar cover of 0.3 to 0.05 mm in thickness, as compared with the silicon cover, is more flexible and excellent in adhesive quality.

iX) The kovar cover having excellent flexibility is capable of automatically compensating for the pressure loss of the charged atmosphere by its flexibility after sealing the compensating side of the substrate, that enables the temperature compensating element to keep its intended heat transfer characteristic and hence to quickly respond to a change in temperature. In the prior art, shown in FIG. 1, the reference space chamber 6 is formed by joining the substrates 1 and 2 with glass paste 5 of a low melting point. When the glass paste 6 fuses, dry air or air of a certain humidity is heated and thereby is enclosed as thinned atmosphere in the reference space chamber. As the result of this, the thin-film heating element 3 cannot sufficiently transfer heat to the charged atmosphere and hence its equilibrium temperature rises making it hard to balance with the sensing side. Furthermore, it requires considerable time to transfer the external ambient temperature to the charged atmosphere thereby affecting the response time. It is also hard to balance the response time with that of the sensing portion.

When the kovar thin plate, having adequate flexibility, is air-tightly attached with fused glass paste to the substrate, it may become dented under the effect of a difference in pressure of the enclosed space and the external pressure to reduce the space volume to the extent at which the density of the air charged in the space is the same as that of the external air. When the charged air has the same density as the external air has, the heating element may have the same equilibrium temperature and heat transferring rate as the sensing portion. Furthermore, decreasing the enclosed space by denting of the cover increases the rate of transferring the external temperature to the compensating sensing element. The silicon (Si) cover does not require flexibility and cannot be sufficiently thinned without decreasing its strength. The enclosed space cannot be decreased in volume and has a low density of air charged therein.

(2) An area for forming a cover (An area to be covered)

i) A bonding pad (electrode) and the upper part of the sensing side are omitted from the covering area.

ii) To join the cover and the sensor's substrate, an adhesive is applied to the area of the cover which corresponds to the peripheral area of the groove formed around the cavity of the sensor's substrate.

iii) The groove surrounding the cavity of the sensor's substrate serves as an adhesive trap for preventing the adhesive from entering into the cavity of the substrate. The groove can be formed together with the respective cavity by a like method, i.e., by anisotropically etching the silicon substrate with an alkaline aqueous solution so that the side wall of the cavity locates at the plane (111) in relation to the plane (100) of the silicon (Si).

iv) It is desirable to provide a groove, not only at the compensating side but also at the sensing side, in order to obtain the stabilized characteristic of the whole system of the sensor with a uniform temperature balance.

v) Frit glass can be used as an adhesive, but it must be heated over 400° C. to fuse and hence it is hard to deal with. In addition, this material may be easily deformed after being cooled to room temperature. It is desirable to use an adhesive with a low melting point. Epoxy resin is available but not desirable because gas contained in epoxy resin may remain in the compensating side cavity, i.e. the atmosphere containing a gas impurity may not represent the intended reference temperature characteristic. Brazing solder such as Au—Su, Si—Sn, Pb—Sn and soldering materials having low melting points are usable.

vi) The substrate and the cover can be easily registered by matching a register mark put on the surface of the substrate with a register hole made in the cover.

(3) Method of manufacturing the cover i) Adhesive is coated on a given area of a thin kovar cover of 0.3 to 0.05 mm in thickness.

ii) Unnecessary parts are removed by photo etching.

iii) The cover is heated and pressed to the substrate of the sensor to form a complete assembly.

iv) A covering can be attached to one substrate chip as well as one substrate wafer. For this purpose a register hole and an outer frame are provided on the materials.

v) The internal volume of the temperature-compensating portion of the substrate to be enclosed by the cover shall be as small as possible to enable the portion to quickly adapt itself to the external temperature of the cover. This is a necessary condition for temperature compensation. It is desirable to attach a flat cover to the substrate with an adhesive layer of not less than 10 μm in thickness to eliminate the possibility of its inner surface coming in contact with the element of the compensating portion. The fear still remains the cover and the element coming in contact, the cover being partially thinned at its inside surface by etching or bent by pressing or being formed into a dome by electroforming.

Figure 6A:
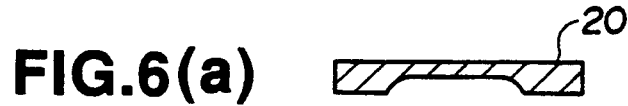
FIGS. 6(a), 6(b) and 6(c) are sectional side views of respective modifications of the covering members.
Figure 6B:
Figure 6C:

FIG. 6(a) shows an example of the cover member having an inside surface partially shaved by etching, FIG. 6(b) shows an example of the press-bent cover and FIG. 6(c) shows an example of a dome-shaped cover formed by electroforming (plating).

Referring to FIG. 6(a), the covering member having a thinned wall for enclosing the compensating portion has an flexibility and easily caves in as previously described. This is effective to adjust the density of the charged air in the enclosed portion to the density of the external air.

Figure 7:
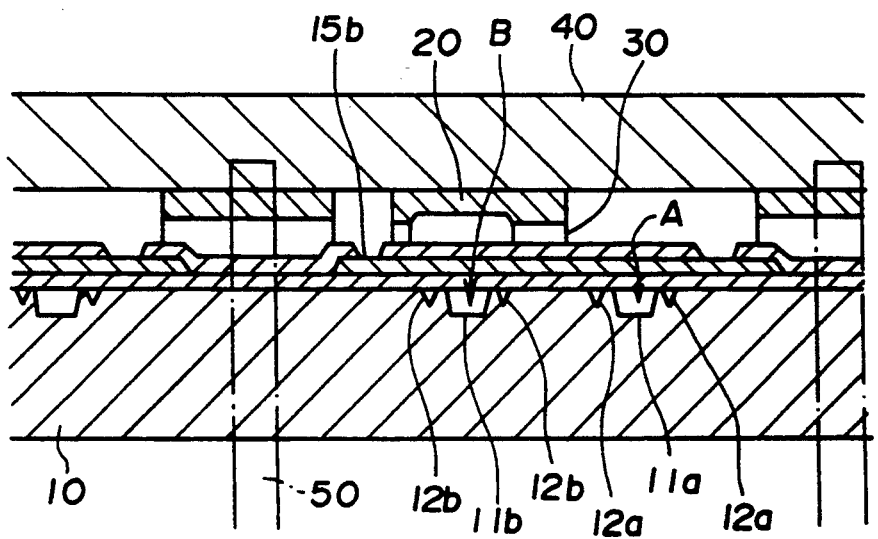
FIG. 7 is a sectional view (taken on line VII—VII of FIG. 8) of the essential part of a sensor for explaining an example of a method for manufacturing the sensor according to the present invention.
Figure 8:
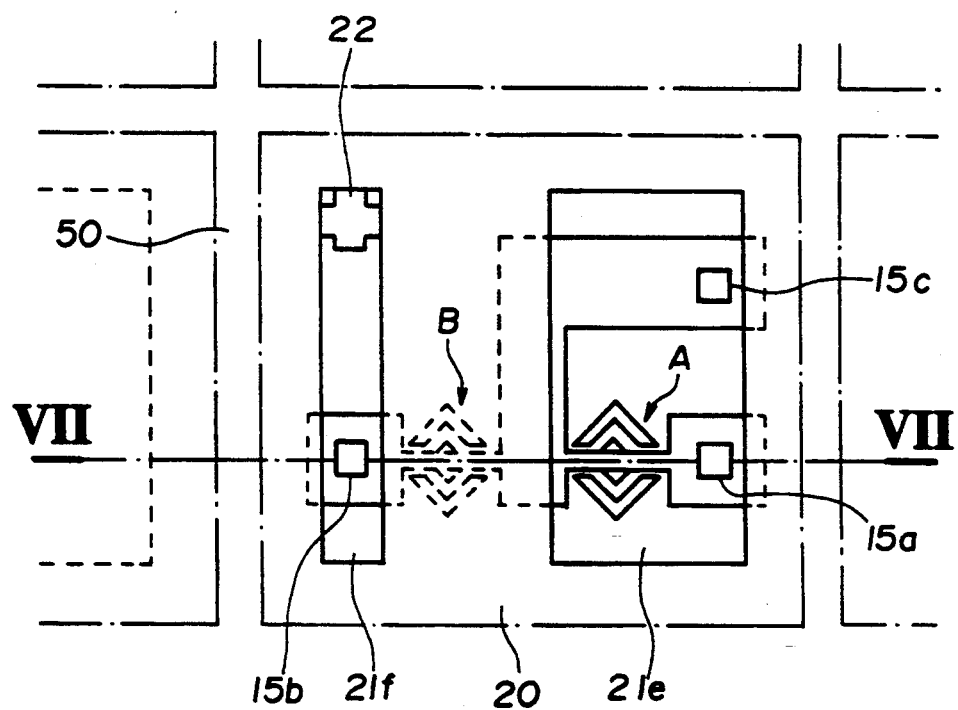
FIG. 8 is a plane view of a sensor before an adhesive tape is attached thereto for dicing.

FIGS. 7 and 8 are views for explaining an embodiment of a sensor manufacturing method according to the present invention. In FIGS. 7 and 8, numeral 40 designates a dicing tape with adhesive and numeral 50 designates a dicing line showing the position of a chip dicing and the width of the dicing saw. Other functioning parts similar to those of the embodiments shown in FIGS. 2 to 5 are denoted by the same reference numerals. FIG. 7 is a sectional view taken along line VII—VII of FIG. 8, wherein the essential part of the sensor comprising the substrate 10 and a covering member 20, formed by the previously described method, is shown as stuck at the covering member side to an adhesive tape 40 for semiconductor chip dicing.

FIG. 8 is a plane view of a sensor's substrate 10 with a covering member 20 air-tightly bonded thereto, which shall be attached to the adhesive tape 40 for chip dicing. As previously described, in the manufacturing process, a large number of sensors are formed on a substrate 10. Accordingly, a pair of gas sensing portions A and a temperature compensating portion B are cut out for use as sensor chips. The known art disclosed in the Japanese publication of unexamined patent applications 3-92754 provides that a shield cover be attached to the substrate to protect the sensing and compensating portions against the effect of water used for the washing of a dicing saw during the chip's separation. This shield cover, however, cannot completely protect the sensor because of the electrode padding portion 9 being exposed.

On the contrary, according to the present invention it is possible to completely protect the sensor from the effect of washing because the electrode padding portion 9 is also enclosed by the adhesive tape 40 for semiconductor chip dicing.

Referring to FIG. 7, the covering member 20 having notches 21e and 21f opposed to an area surrounding the electrode pad and an area of the atmospheric (humidity) sensor, respectively, on the substrate 10 is adhesively attached onto the substrate 10 and then attached to the adhesive tape 40 fop semiconductor chip dicing. The substrate is now separated into unit chips along the dicing lines 50 shown in FIG. 8. The combination of the covering member and the adhesive dicing tape allows for a series of operations for manufacturing the sensors to be effectively carried,out with no effect of the water used for washing during the semiconductor chip separation using a dicing saw.

I claim:

1. A sensor comprising a substrate having at least two cavities formed therein and at least two sensing portions bridged over the respective cavities, said sensing portions comprising a first sensing unit being exposed to ambient atmosphere for sensing the state of the atmosphere and a second sensing unit being air-tightly enclosed by a cover member and usable for temperature compensation, characterized in that the cover member is made of a thin flat plate and is air-tightly joined with the substrate by means of a solid adhesive layer formed around the boundary of the second sensing unit.

2. A sensor according to claim 1, characterized in that the cover member has an open hole opposite to the first sensing unit.

3. A sensor according to claim 1 or 2, characterized in that the substrate has a register mark on its surface and the cover member has a register hole matching the location of the register mark on the surface of the substrate.

4. A sensor according to claim 1, characterized in that a groove is provided at least around the cavity forming the second sensing unit on the substrate.

5. A sensor according to claim 1, characterized in that the cover member has a concave portion at its inner surface opposite to the second sensing unit.

6. A sensor according to claim 1, characterized in that the cover member is made of a flexible material.

7. A sensor according to claim 6, wherein the flexible material comprises koval.

8. A sensor according to claim 6, wherein the flexible material comprises one of the group of materials consisting of stainless steel, nickel and nichrome.

9. A method of manufacturing a sensor having a substrate, a plurality of cavities formed therein and sensing portions bridged over the respective cavities, wherein a first sensing unit is exposed to ambient atmosphere for sensing the state of the atmosphere and a second sensing unit is air-tightly enclosed by a cover member and used for temperature compensation, said method comprising the steps of:

air-tightly attaching the cover member to the substrate by means of a solid adhesive layer formed around the periphery of the second sensing unit, attaching an adhesive tape for dicing to the cover member, and then separating a unit sensor chip having a set of sensing portions from the substrate.

10. A method according to claim 9, wherein said step of air-tightly attaching the cover member to the substrate is performed prior to the step of attaching an adhesive tape for dicing to the cover member.

11. A sensor comprising:
a substrate having at least two cavities formed therein;
at least two sensing portions bridged over the respective cavities, a first of said sensing portions being exposed to ambient atmosphere; and
a cover member made of .a thin flat plate and air-tightly joined with the substrate by means of a solid adhesive layer formed around the boundary of a second of said sensing portions to air-tightly enclose the second of said sensing portions.

12. A sensor according to claim 11, wherein the cover member is made of a flexible material.

13. A sensor according to claim 12, wherein the flexible material comprises koval.

14. A sensor according to claim 12, wherein the flexible material comprises one of the group of materials consisting of stainless steel, nickel and nichrome.

* * * * *